United States Patent

Kitazawa et al.

Patent Number: 5,594,012
Date of Patent: Jan. 14, 1997

[54] AMINO ACID DERIVATIVES AND ANTI-ACTIVE OXYGEN AGENTS

[75] Inventors: Manabu Kitazawa; Keiji Iwasaki, both of Kawasaki, Japan

[73] Assignee: Ajinomoto Co., Inc., Tokyo, Japan

[21] Appl. No.: 284,668

[22] PCT Filed: Dec. 20, 1993

[86] PCT No.: PCT/JP93/01842

§ 371 Date: Oct. 6, 1994

§ 102(e) Date: Oct. 6, 1994

[87] PCT Pub. No.: WO94/14755

PCT Pub. Date: Jul. 7, 1994

[30] Foreign Application Priority Data

Dec. 21, 1992 [JP] Japan ........... 4-340426

[51] Int. Cl.$^6$ .......... A61K 31/44; C07D 215/50; C07C 229/14; C07C 251/18

[52] U.S. Cl. .......... 514/345; 514/399; 514/415; 514/638; 514/646; 514/844; 546/288; 548/335.5; 548/506; 564/280; 564/428

[58] Field of Search .......... 514/844, 345, 514/638, 646, 657, 415, 399; 546/288; 564/428, 280; 548/335.5, 506

[56] References Cited

U.S. PATENT DOCUMENTS 4,771,060 9/1988 Nakagawa .................. 514/365
4,792,355 12/1988 Siegl .................. 106/14.15

FOREIGN PATENT DOCUMENTS 266189 3/1989 Germany .
222416 11/1985 Japan .

OTHER PUBLICATIONS

McIntire FC. (1947). J. Am. Chem. Soc. 69(6) 1377–1380.

*Primary Examiner*—C. Warren Ivy
*Assistant Examiner*—Evelyn Huang
*Attorney, Agent, or Firm*—Oblon, Spivak, McClelland, Maier & Neustadt, P.C.

[57] ABSTRACT

A novel anti-active oxygen agent which comprises as active ingredient an amino acid derivative represented by the following general formula (I):

$$Ar-X-\underset{R}{CH}-(CH_2)_n-Y \qquad (I)$$

wherein Ar represents a 2-hydroxyphenyl, 2-hydroxy-1-naphthyl or pyridyl group, and one or more of the hydrogen atoms attached to the aromatic ring of these groups may be substituted with a halogen atom, or an alkyl, hydroxyl, hydroxyalkyl, nitro, alkoxyl or carboxyl group; R represents the side chain of an amino acid; X represents $-CH_2-NH-$ or $-CH=N-$; Y represents a hydrogen atom, $-COOR^1$, $-SO_3H$, $-CON(R^2)R^3$, $-CONHCH(R^5)COOR^4$ or $-CH_2OH$ (where each of $R^1$ to $R^4$ represents a hydrogen atom or an alkyl group, and $R^5$ represents the side chain of an amino acid); and n represents an integer of 0 or 1;

or its salt, and which inhibits generation of active oxygen species, has a high safety and can be prepared at relatively low costs.

22 Claims, No Drawings

AMINO ACID DERIVATIVES AND ANTI-ACTIVE OXYGEN AGENTS

This application is the national phase of PCT/JP93/01842 filed on Dec. 20, 1993.

TECHNICAL FIELD

This invention relates to novel anti-active oxygen agents, and more specifically to anti-active oxygen agents which inhibit the generation of active oxygen and thus produce desired effects including preventive activities against skin-aging or other diseases.

BACKGROUND ART

In recent years, various disorders and diseases caused by active oxygen species such as superoxide anion radical ($O_2^-$), hydroxyl radical (.OH), singlet oxygen ($^1O_2$), and peroxide lipid have been reported. It is known that active oxygen species are deeply implicated as a cause in aging, canceration, pigmentation, inflammation or other skin disorders induced by the solar rays, particularly UV rays. The implication of active oxygen species in disorders and diseases in living bodies other than skin has also been explained. For example, active oxgen species derived from molecular oxygens added into ischemic tissues by blood reperfusion play an important role in ischemic reperfusion-induced disorders in organs such as heart, enteron, gaster, liver, kidney, and brain. Similarly, active oxygen species generated in living bodies bring about, for example, a wide variety of disorders and diseases such as inflammation, rheumatism, aging, cancer, arteriosclerosis, digestive diseases, kidney diseases, endocrine disorders, lung diseases, shock, disseminated intravascular coagulation syndrome, etc. It has been also reported that active oxygen species are responsible for denaturation and deterioration caused by oxidation of fats and oils in foods.

If the action of active oxygen species in such a wide range including living organs such as skin and foods could be inhibited, these disorders and diseases as well as denaturation and deterioration of foods would be prevented.

Known agents inhibiting the action of active oxygen species include enzyme-based anti-oxydants such as superoxide dismutase (SOD); non-enzyme-based anti-oxydants such as ascorbic acid, tocopherol and glutathione; and vegetable-derived anti-oxydant such as tannin. Recently, some attempts have been reported to inhibit the generation of active oxygen species by capture of metal ions, in view of the fact that metal ions present in living bodies function as catalyst in the generation of active oxygen species (For example, see "Free Radicals in Biology and Medicine", Oxford, Clarendon Press, p. 234, 1989).

Among known agents which inhibit the action of active oxygen species, SOD is limited in use because of its high costs and instability. Many of non-enzyme-based anti-oxydants such as ascorbic acid, tocopherol and glutathione are also instable and insufficient to inhibit the action of active oxygen species. Further, vegetable-derived anti-oxydants such as tannin often suffer from problems of stability, since they are susceptible to hydrolysis, oxydation, etc.

Desferrioxamines are typical compounds capable of capturing metal ions. However, they have so high metal ion capturing capacity for pharmaceutical use that they disturb the balance of metal ions in living bodies and thus invite side effects such as inflammation. Moreover, they have the disadvantage that they can not show sufficient inhibitory effects on the generation of active oxygen species by oral administration. Further, they are difficult to use in cosmetics and foods because of their high costs. Other than desferrioxamines, metal ion chelating agents such as 2,2'-dipyridyl, 1,10-phenanthrolene, and 2,2'-dipyridylamine were examined, but most of them showed toxicity or skin irritation.

An object of this invention is to provide a novel anti-active oxygen agent which inhibits the generation of active oxygen species, ensures a high safety and can be produced at relatively low costs.

DISCLOSURE OF THE INVENTION

This invention relates to an anti-active oxygen agent which comprises as an active ingredient an amino acid derivative represented by the following general formula (I):

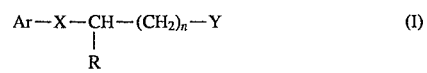

wherein Ar represents a 2-hydroxyphenyl, 2-hydroxy-1-naphthyl or pyridyl group, and one or more of the hydrogen atoms attached to the aromatic ring of these groups may be replaced by a halogen atom, or a C1–6 alkyl, hydroxyl, C1–6 hydroxyalkyl, nitro, C1–6 alkoxyl or carboxyl group, provided that when two or more of the hydrogen atoms are substituted, the substituents may be the same or different; R represents a side chain of an amino acid; X represents —$CH_2$—NH— or —CH=N—; Y represents a hydrogen atom, —$COOR^1$, —$SO_3H$, —$CON(R^2)R^3$, —$CONHCH(R^5)COOR^4$ or —$CH_2OH$ (where each of $R^1$ to $R^4$ represents a hydrogen atom or a C1–6 alkyl group, and $R^5$ represents a side chain of an amino acid); and n represents an integer of 0 or 1;
or a salt thereof.

Among those represented by the general formula (I), the compounds represented by the following general formula (II) or (III) are novel and have never been described yet.

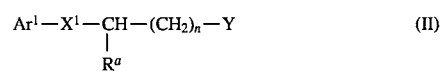

wherein $Ar^1$ represents a 2-hydroxyphenyl group, and one or more of the hydrogen atoms attached to the aromatic ring of this group may similarly be substituted with a halogen atom, or an alkyl, hydroxyl, hydroxyalkyl, nitro, alkoxyl or carboxyl group as defined above in the general formula (I); $R^a$ represents the side chain of valine, leucine, isoleucine, glutamic acid, glutamine, asparagine, arginine, lysine, methionine, threonine, tyrosine, tryptophan, homoserine or 3,4-dihydroxyphenylalanine, or a hydrogen atom; $X^1$ represents —$CH_2$—NH—; and each of Y and n has the same meaning as defined above in the general formula (I).

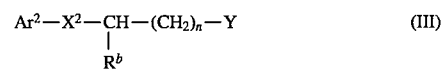

wherein $Ar^2$ represents a 2-hydroxy-1-naphthyl group, and one or more of the hydrogen atoms attached to the aromatic ring of this group may similarly be substituted with a halogen atom, or an alkyl, hydroxyl, hydroxyalkyl, nitro, alkoxyl or carboxyl group as defined above in the general formula (I); $R^b$ represents the side chain of leucine, isoleucine, glutamic acid, glutamine, aspartic acid, asparagine, arginine, histidine, lysine, methionine, cysteine, serine, threonine, tyrosine, phenylalanine, tryptophan, homoserine or 3,4-dihydroxyphenylalanine; $X^2$ represents —CH=N—; and each of Y and n has the same meaning as defined above in the general formula (I).

In the general formula (I), Ar is preferably a 2-hydroxyphenyl, 2-hydroxy-5-chlorophenyl, 2-hydroxy-5-nitrophenyl, 2-hydroxy-1-naphthyl or 2-methyl-3-hydroxy-5-hydroxymethyl-4-pyridyl group in view of active oxygen inhibitory effects. The side chain (R) of an amino acid is preferably the side chain of histidine, serine, homoserine, tyrosine, 3,4-dihydroxyphenylalanine, glutamic acid, aspartic acid, lysine, threonine, glutamine, asparagine, arginine, phenylalanine, tryptophan, etc., also in view of the active oxygen inhibitory effects.

The compounds represented by the general formula (I) can be easily prepared, for example, according to the following scheme:

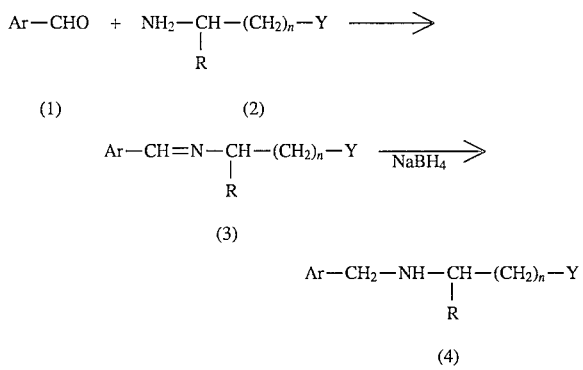

wherein Ar, Y, R and n have the same meanings as defined above.

Compound (3) can be easily obtained by reacting a 2-hydroxy aromatic aldehyde (1) such as salicylaldehyde with an amino acid, an amino alcohol obtained by reducing an amino acid, amino acid ester or amino acid amide, these being collectively referred to as Compound (2), in the presence or absence of a solvent. Compound (4) can be derived by adding a hydrogenating agent such as sodium borohydride during or after the reaction between Compound (1) and Compound (2).

Though the anti-active oxygen compounds of the general formula (I) according to this invention may be directly administered to active oxygen generating systems, for example, intravenously, skin-topically, etc., they are usually incorporated in cosmetics such as lotion and cream; pharmaceuticals such as anti-inflammatory agent and antiarteriosclerotic agent; and foods such as edible oil. For use as the anti-skin aging component in cosmetics for example, they should be naturally comprised in an amount producing anti-skin aging activities, and may be comprised in an amount of, for example, 0.1 to 10% of the total weight of the cosmetics. For pharmaceutical use in human bodies, they should be naturally administered in an amount producing an intended effect, and may be administered in an amount of, for example, 0.1 to 1000 mg/day per adult. In order to prevent denaturation or deterioration of foods, they may be similarly added to the foods in an amount of 0.1 to 10% of the weight thereof. Otherwise, the anti-active oxygen compounds according to this invention may be formulated into special anti-skin aging preparations, e.g., in the form of ointment, instead of being incorporated in cosmetics.

BEST MODE FOR CARRING OUT THE INVENTION

This invention may be better understood by reference to the following examples including synthesis examples, test examples and use examples, which are not intended to limit the scope of the invention.

SYNTHESIS EXAMPLE 1

To 20 ml of a 2N aqueous solution of sodium hydroxide in which 5 g of L-histidine had been dissolved, 3.5 ml of salicylaldehyde and 0.4 g of sodium borohydride were successively added. After stirring for 1 hour, additional 3.5 ml of salicylaldehyde and 0.4 g of sodium borohydride were successively added. After stirring at room temperature for 1 hour, the unsolubles were filtered out and the filtrate was extracted with diethyl ether. The pH was adjusted to 6 with hydrochloric acid to give 8 g of N-(2-hydroxybenzyl)-L-histidine.

The measured results of the melting point, mass spectrum (FAB-MS) and NMR spectrum of the resulting compound are listed in Table 1 below.

SYNTHESIS EXAMPLES 2 TO 26

In the same way as described in Synthesis Example 1, the compounds shown in Table 1 were prepared. The measured results of the melting point, mass spectrum and NMR spectrum of each compound are also listed in Table 1.

TABLE 1

$Ar-CH_2-NH-CH(R_{15})-(CH_2)_n-Y$

| Syn ex. | Ar | $R_{15}$ | n | Y | m.p. | MS | NMR |
|---|---|---|---|---|---|---|---|
| 1 | (2-hydroxyphenyl, OH) | imidazolyl-CH₂ (NH, N) | 0 | —COOH | 224~225° C. | m/z: 262(M + H) | (D₂O+NaOD)δ(ppm): 2.92(t, 2H), 3.42(t, 1H), 3.60(dd, 2H), 6.56(t, 1H), 6.68(d, 1H), 6.88(s, 1H), 7.08(t, 1H), 7.13(d, 1H), 7.59(s, 1H) |
| 2 | (2-hydroxyphenyl, OH) | —CH₂OH | 0 | —COOH | 224~226° C. | m/z: 212(M + H) | (D₂O+NaOD)δ(ppm): 3.31(t, 1H), 3.71(dd, 2H), 3.76(dd, 2H), 6.60(t, 1H), 6.66(d, 1H), 7.12(t, 1H), 7.19(d, 1H) |

TABLE 1-continued $$Ar-CH_2-NH-CH(R_{15})-(CH_2)_n-Y$$

| Syn ex. | Ar | $R_{15}$ | n | Y | m.p. | MS | NMR |
|---|---|---|---|---|---|---|---|
| 3 | 2-hydroxyphenyl | –CH₂CH₂CH₂OH | 0 | –COOH | 189~190° C. | m/z: 226(M + H) | (D₂O+NaOD)δ(ppm): 1.75~1.97(m, 2H), 3.31(t, 1H), 3.55(t, 2H), 4.00(d, 2H), 6.80(t, 1H), 6.87(d, 1H), 7.18(t, 1H), 7.25(d, 1H) |
| 4 | 2-hydroxyphenyl | –CH₂–(4-hydroxyphenyl) | 0 | –COOH | 251~252° C. | m/z: 288(M + H) | ((CD₃)₂SO)δ(ppm): 2.89(m, 2H), 3.34(t, 1H), 3.73(dd, 2H), 6.68(d, 2H), 6.76(dd, 2H), 7.04(d, 2H), 7.05(t, 1H), 7.13(t, 1H) |
| 5 | 2-hydroxyphenyl | –CH₂CH₂COOH | 0 | –COOH | | m/z: 254(M + H) | (D₂O+NaOD)δ(ppm): 1.83(m, 2H), 2.18(t, 2H), 3.12(t, 1H), 3.58(dd, 2H), 6.56(t, 1H), 6.60(d, 1H), 7.07(t, 1H), 7.11(d, 1H) |
| 6 | 2-hydroxyphenyl | CH₃ | 0 | –COOH | | m/z: 196(M + H) | (D₂O+NaOD)δ(ppm): 1.36(d, 3H), 3.33(q, 1H), 3.72(dd, 2H), 6.67(t, 1H), 6.73(d, 1H), 7.20(t, 1H), 7.26(d, 1H) |
| 7 | 2-hydroxyphenyl | –CH₂–phenyl | 0 | –COOH | | m/z: 272(M + H) | (D₂O+NaOD)δ(ppm): 2.94(t, 2H), 3.43(t, 1H), 3.60(dd, 2H), 6.55(t, 1H), 6.61(d, 1H), 7.04(d, 2H), 7.32(m, 4H) |
| 8 | 2-hydroxyphenyl | CH(CH₃)₂ | 0 | –COOH | | m/z: 224(M + H) | (D₂O+NaOD)δ(ppm): 1.00(dd, 6H), 1.89(m, 1H), 2.97(d, 1H), 3.60(dd, 2H), 6.60(t, 1H), 6.66(d, 1H), 7.10(t, 1H), 7.18(d, 1H) |
| 9 | 2-hydroxyphenyl | H | 0 | –COOH | | m/z: 182(M + H) | (D₂O+NaOD)δ(ppm): 3.19(s, 2H), 3.63(s, 2H), 6.58(t, 1H), 6.62(d, 1H), 7.10(t, 1H), 7.18(d, 1H) |
| 10 | 2-hydroxyphenyl | H₃C–CH(OH)– | 0 | –COOH | | m/z: 226(M + H) | (D₂O+NaOD)δ(ppm): 1.20(d, 3H), 3.05(d, 1H), 3.62(dd, 2H), 3.85(m, 1H), 6.58(t, 1H), 6.64(d, 1H), 7.10(t, 1H), 7.15(d, 1H) |
| 11 | 2-hydroxyphenyl | H | 0 | –CONH₂ | | m/z: 181(M + H) | (D₂O+NaOD)δ(ppm): 3.31(s, 2H), 3.67(s, 2H), 6.59(t, 1H), 6.64(d, 1H), 7.12(t, 1H), 7.20(d, 1H) |
| 12 | 2-hydroxyphenyl | H | 1 | –COOH | | m/z: 196(M + H) | (D₂O+NaOD)δ(ppm): 2.47(t, 2H), 2.86(t, 2H), 3.70(s, 2H), 6.65(t, 1H), 6.70(d, 1H), 7.14(t, 1H), 7.20(d, 1H) |
| 13 | 2-hydroxyphenyl | H | 1 | –SO₃H | | m/z: 230(M – H) | (D₂O)δ(ppm): 3.32(t, 2H), 3.50(t, 2H), 4.32(s, 2H), 7.05(m, 2H), 7.41(m, 2H) |
| 14 | 2-hydroxyphenyl | –CH₂CH₂OH | 0 | –H | | m/z: 168(M + H) | (D₂O+NaOD)δ(ppm): 2.73(t, 2H), 3.67(s, 2H), 3.70(s, 2H), 6.56(t, 1H), 6.64(d, 1H), 7.12(t, 1H), 7.18(d, 1H) |

TABLE 1-continued

| | | Ar—CH$_2$—NH—CH(R$_{15}$)—(CH$_2$)$_n$—Y | | | | | |
|---|---|---|---|---|---|---|---|
| Syn ex. | Ar | R$_{15}$ | n | Y | m.p. | MS | NMR |
| 15 | 2-methylphenol (o-cresol) | CH$_2$-(imidazole) | 0 | —H | | m/z: 218(M + H) | (D$_2$O+NaOD)δ(ppm): 2.78(tt, 4H), 3.63(s, 2H), 6.52(t, 1H), 6.60(d, 1H), 6.82(s, 1H), 7.07(t, 1H), 7.14(d, 1H), 7.57(s, 1H) |
| 16 | pyridoxine | H | 0 | —COOH | | m/z: 226(M + H) | |
| 17 | pyridoxine | CH$_3$ | 0 | —COOH | | | (D$_2$O+NaOD)δ(ppm): 1.29(d, 3H), 2.37(s, 3H), 3.30(q, 1H), 3.82(dd, 2H), 4.62(t, 2H), 7.56(s, 1H) |
| 18 | pyridoxine | CH$_2$OH | 0 | —COOH | 221~223° C. (2Na 塩として) | m/z: 301(M + H) | (D$_2$O)δ(ppm): 2.49(s, 3H), 3.72(t, 1H), 4.00(dd, 2H), 4.45(dd, 2H), 4.70(s, 2H), 7.62(s, 1H) |
| 19 | pyridoxine | CH(CH$_3$)OH | 0 | —COOH | | m/z: 271(M + H) | (D$_2$O+NaOD)δ(ppm): 1.21(d, 3H), 2.34(s, 3H), 3.10(d, 1H), 3.80(dd, 2H), 3.84(m, 1H), 4.59(s, 2H), 7.53(s, 1H) |
| 20 | pyridoxine | CH$_2$COOH | 0 | —COOH | | m/z: 285(M + H) | |
| 21 | pyridoxine | CH$_2$CONH$_2$ | 0 | —COOH | | m/z: 284(M + H) | |
| 22 | pyridoxine | CH$_2$-(imidazole) | 0 | —COOH | | m/z: 307(M + H) | (D$_2$O)δ(ppm): 2.51(s, 3H), 3.33(d, 2H), 3.88(t, 1H), 4.42(dd, 2H), 4.69(s, 2H), 7.30(s, 1H), 7.68(s, 1H), 7.75(s, 1H) |
| 23 | pyridoxine | CH$_2$-(imidazole) | 0 | —CONH$_2$ | | m/z: 306(M + H) | |
| 24 | pyridoxine | (CH$_2$)$_3$—NH—C(=NH)NH$_2$ | 0 | —COOH | | m/z: 326(M + H) | |

TABLE 1-continued

Ar—CH$_2$—NH—CH(R$_{15}$)—(CH$_2$)$_n$—Y

| Syn ex. | Ar | R$_{15}$ | n | Y | m.p. | MS | NMR |
|---|---|---|---|---|---|---|---|
| 25 | 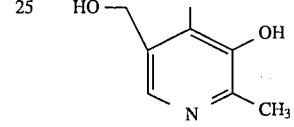 | 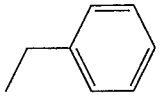 | 0 | —COOH | | m/z: 317(M + H) | (D$_2$O+NaOD)δ(ppm): 2.28(s, 3H), 2.87(m, 2H), 3.44(t, 1H), 3.70(dd, 2H), 4.40(dd, 2H), 7.20(d, 2H), 7.27(t, 1H), 7.30(d, 2H) 7.43(s, 1H) |
| 26 | 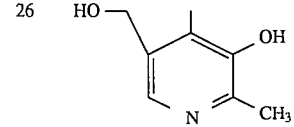 |  | 0 | —COOH | | m/z: 333(M + H) | |

SYNTHESIS EXAMPLE 27

To 220 ml of absolute ethanol were added 1.6 g of L-histidine and 2.6 g of 2-hydroxy-1-naphthaldehyde, and the mixture was stirred for 5 days to give 2.4 g of N-(2-hydroxy-1-naphthal)-L-histidine.

The measured results of the melting point, mass spectrum and NMR spectrum of the resulting compound are listed in Table 2 below.

SYNTHESIS EXAMPLE 28 TO 67

In the same way as described in Synthesis Example 27, the compounds shown in Table 2 were prepared. The measured results of the melting point, mass spectrum and NMR spectrum of each compound are listed in Tables 2 and 3.

TABLE 2

Ar—CH=N—CH(R$_{16}$)—Y

| Syn. ex. | Ar | R$_{16}$ | Y | m.p. | MS | NMR |
|---|---|---|---|---|---|---|
| 27 | 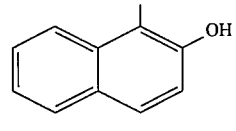 | 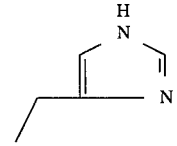 | —COOH | 171~173° C. | m/z: 310(M + H) | ((CD$_3$)$_2$SO) δ(ppm): 3.14(dd, 2H), 4.69(t,1H), 6.71(d, 1H), 6.86(s, 1H), 7.20(t, 1H), 7.40(t, 1H), 7.62(s, 1H), 7.64(d, 1H), 7.71(d, 1H), 7.88(d, 1H), 8.85(s, 1H) |
| 28 | 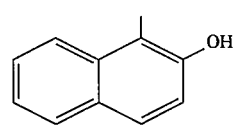 | 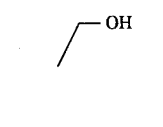 | —COOH | 190~191° C. | m/z: 260(M + H) | ((CD$_3$)$_2$SO)δ(ppm): 3.88(d, 2H), 4.51(t, 1H), 6.82(d, 1H), 7.20(t, 1H), 7.42(t, 1H), 7.63(d, 1H), 7.73(d, 1H), 8.08(d, 1H), 9.05(s, 1H) |
| 29 | 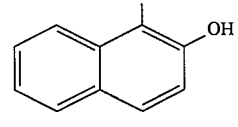 | 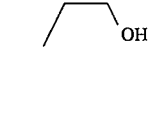 | —COOH | 183~184° C. | m/z: 274(M + H) | ((CD$_3$)$_2$SO)δ(ppm): 2.09(m, 2H), 3.58(dt, 2H), 4,56(t, 1H), 6.78(d, 1H), 7.24(t, 1H), 7.45(t, 1H), 7.69(d, 1H), 7.78(d, 1H), 8.08(d, 1H), 9.11(s, 1H) |
| 30 | 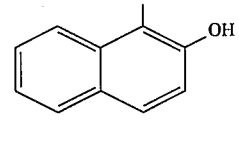 | 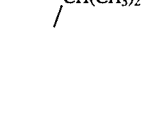 | —COOH | 187~188° C. | m/z: 272(M + H) | ((CD$_3$)$_2$SO)δ(ppm): 0.96(d, 6H), 2.32(m, 1H), 4.33(t, 1H), 6,78(d, 1H), 7.22(t, 1H), 7.45(t, 1H), 7.68(d, 1H), 7.79(d, 1H), 8.08(d, 1H), 9.14(s, 1H) |
| 31 | 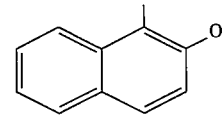 | 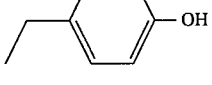 | —COOH | 156~158° C. | m/z: 336(M + H) | ((CD$_3$)$_2$SO)δ(ppm): 3.07(d, 2H), 4.63(t, 1H), 6.63(d, 2H), 6,75(d, 1H), 7.02(d, 2H), 7.22(t, 1H), 7.40(t, 1H), 7.65(d, 1H), 7.76(d, 1H), 7.88(d, 1H), 9.23(s, 1H) |

TABLE 2-continued

| | | Ar—CH=N—CH($R_{16}$)—Y | | | |
|---|---|---|---|---|---|
| Syn. ex. | Ar | $R_{16}$ | Y | m.p. | MS | NMR |
| 32 | 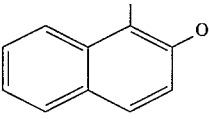 | 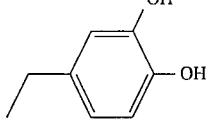 | —COOH | 165~166° C. | m/z: 352(M+H) | ((CD$_3$)SO)δ(ppm): 3.09(m, 2H), 4.60(t, 1H), 6.46(d, 1H), 6.61(s, 1H), 6.62(d, 1H), 6.74(d, 1H), 7.21(t, 1H), 7.39(t, 1H), 7.65(d, 1H), 7.75(d, 1H), 7.89(d, 1H), 8.88(s, 1H) |
| 33 | 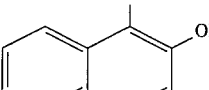 | 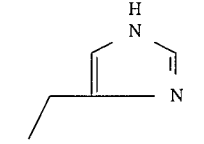 | —CH$_2$OH | 169~170° C. | m/z: 296(M+H) | ((CD$_3$)$_2$SO)δ(ppm): 2.95(m, 2H), 3.63(m, 1H), 3.97(d, 2H), 6.68(s, 1H), 6.86(s, 1H), 7,15(t, 1H), 7.41(t, 1H), 7.55(s, 1H), 7.63(d, 1H), 7.69(d, 1H), 7.95(d, 1H), 8.95(s, 1H) |
| 34 | 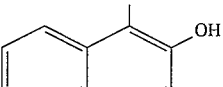 |  | —COOH | | m/z: 230(M+H) | ((CD$_3$)$_2$SO)δ(ppm): 4.48(s, 2H), 6.74(d, 1H), 7.20(t, 1H), 7.43(t, 1H), 7.63(d, 1H), 7,74(d, 1H), 8.01(d, 1H), 9.06(s, 1H) |
| 35 | 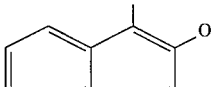 | 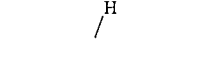 | —CONH$_2$ | | m/z: 229(M+H) | |
| 36 | 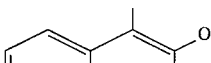 | 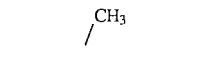 | —COOH | | m/z: 244(M+H) | ((CD$_3$)$_2$SO)δ(ppm): 1.58(d, 3H), 4.56(q, 1H), 6.79(d, 1H), 7.23(t, 1H), 7.45(t, 1H), 7.67(d, 1H), 7.77(d, 1H), 8.10(d, 1H), 9.18(s, 1H) |
| 37 | 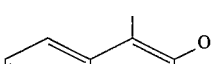 | 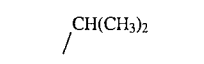 | —CH$_2$OH | | m/z: 258(M+H) | |
| 38 | 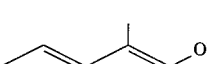 | 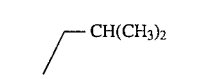 | —COOH | | m/z: 286(M+H) | ((CD$_3$)$_2$SO)δ(ppm): 0.97(d, 6H), 1.64(m, 1H), 1.81(t, 2H), 4.48(t, 1H), 6.79(d, 1H), 7.23(t, 1H), 7.45(t, 1H), 7.67(d, 1H), 7.77(d, 1H), 8.10(d, 1H), 9.20(s, 1H) |
| 39 | 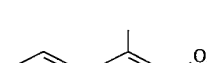 | 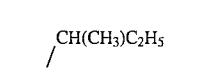 | —COOH | | m/z: 286(M+H) | ((CD$_3$)$_2$SO)δ(ppm): 0.96(t, 3H), 0.97(d, 3H), 1.24(m, 1H), 1.51(m, 1H), 2.08(m, 1H), 4.36(m, 1H), 6.78(d, 1H), 7.21(t, 1H), 7.44(t, 1H), 7.66(d, 1H), 7.77(d, 1H), 8.08(d, 1H), 9.14(s, 1H) |
| 40 | 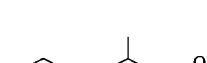 | 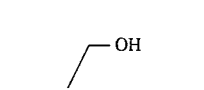 | —COOCH$_3$ | | m/z: 274(M+H) | |
| 41 |  | 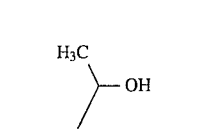 | —COOH | | m/z: 274(M+H) | ((CD$_3$)$_2$SO)δ(ppm): 1.17(d, 3H), 4.30(m, 1H), 4.34(d, 1H), 6.70(d, 1H), 7.19(t, 1H), 7.41(t, 1H), 7.62(d, 1H), 7.72(d, 1H), 7.99(d, 1H), 9.00(s, 1H) |

TABLE 2-continued

Ar—CH=N—CH(R₁₆)—Y

| Syn. ex. | Ar | R₁₆ | Y | m.p. | MS | NMR |
|---|---|---|---|---|---|---|
| 42 | 2-naphthol (1-substituted) | —CH₂CH₂—SCH₃ | —COOH | | m/z: 304(M+H) | ((CD₃)₂SO)δ(ppm): 2.09(s, 3H), 2.20(m, 2H), 2.55(t, 2H), 4.56(t, 1H), 6.83(d, 1H), 7.27(t, 1H), 7.48(t, 1H), 7.69(d, 1H), 7.80(d, 1H), 8.12(d, 1H), 9.21(s, 1H) |
| 43 | 2-naphthol (1-substituted) | —CH₂—COOH | —COOH | | m/z: 288(M+H) | ((CD₃)₂SO)δ(ppm): 2.99(t, 2H), 4.70(t, 1H), 6.78(d, 1H), 7.24(t, 1H), 7.46(t, 1H), 7.68(d, 1H), 7.77(d, 1H), 8.07(d, 1H), 9.17(s, 1H) |
| 44 | 2-naphthol (1-substituted) | —CH₂—CONH₂ | —COOH | | m/z: 287(M+H) | ((CD₃)₂SO)δ(ppm): 2.83(t, 2H), 4.71(t, 1H), 6.77(d, 1H), 7.23(t, 1H), 7.45(t, 1H), 7.66(d, 1H), 7.75(d, 1H), 8.04(d, 1H), 9.10(s, 1H) |
| 45 | 2-naphthol (1-substituted) | —CH₂-(imidazol-4-yl) | —COOCH₃ | | m/z: 324(M+H) | |
| 46 | 2-naphthol (1-substituted) | —CH₂-(imidazol-4-yl) | —H | | m/z: 266(M+H) | |
| 47 | 2-naphthol (1-substituted) | —CH₂CH₂CH₂—COOH | —COOH | | m/z: 302(M+H) | ((CD₃)₂SO)δ(ppm): 2.12(m, 1H), 2.29(m, 1H), 2.33(t, 2H), 4.45(t, 1H), 6.80(d, 1H), 7.25(t, 1H), 7.45(t, 1H), 7.67(d, 1H), 7.78(d, 1H), 8.09(d, 1H), 9.17(s, 1H) |
| 48 | 2-naphthol (1-substituted) | —CH₂CH₂—COOCH₃ | —COOH | | m/z: 316(M+H) | ((CD₃)₂SO)δ(ppm): 2.15(m, 1H), 2.29(m, 1H), 2.43(t, 2H), 3.56(s, 3H), 4.48(t, 1H), 6.85(d, 1H), 7.26(t, 1H), 7.49(t, 1H), 7.70(d, 1H), 7.82(d, 1H), 8.11(d, 1H), 9.20(s, 1H) |
| 49 | 2-naphthol (1-substituted) | —CH₂CH₂—COOCH₃ | —COOCH₃ | | m/z: 330(M+H) | ((CD₃)₂SO)δ(ppm): 2.20(m, 1H), 2.30(m, 1H), 2.43(t, 2H), 3.56(s, 3H), 3.75(s, 3H), 4.57(t, 1H), 6.90(d, 1H), 7.28(t, 1H), 7.50(t, 1H), 7.73(d, 1H), 7.83(d, 1H), 8.13(d, 1H), 9.27(s, 1H) |
| 50 | 2-naphthol (1-substituted) | —CH₂CH₂—CONHOH | —COOH | | m/z: 317(M+H) | |
| 51 | 2-naphthol (1-substituted) | —CH₂CH₂CH₂—CONH₂ | —COOH | | m/z: 301(M+H) | ((CD₃)₂SO)δ(ppm): 2.06(m, 1H), 2.18(t, 2H), 2.25(m, 1H), 4.48(t, 1H), 6.81(d, 1H), 7.23(t, 1H), 7.46(t, 1H), 7.69(d, 1H), 7.77(d, 1H), 8.10(d, 1H), 9.16(s, 1H) |

TABLE 2-continued
| Syn. ex. | Ar | R₁₆ | Y | m.p. | MS | NMR |
|---|---|---|---|---|---|---|
| 52 | 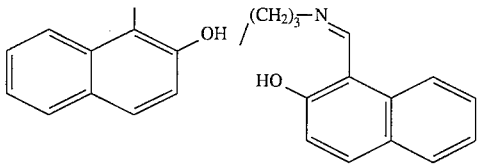 | 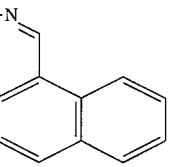 | —COOH | | m/z: 455(M + H) | |
| 53 | 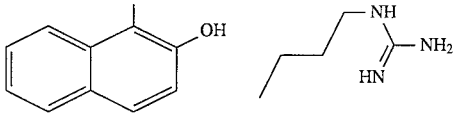 | 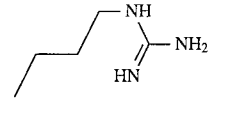 | —COOH | | m/z: 329(M + H) | ((CD₃)₂SO)δ(ppm): 1.57(d, 2H), 1.90(m, 2H), 3.14(t, 2H), 4.15(t, 1H), 6.64(d, 1H), 7.13(t, 1H), 7.37(t, 1H), 7.56(d, 1H), 7.63(d, 1H), 8.00(d, 1H), 8.94(s, 1H) |
| 54 | 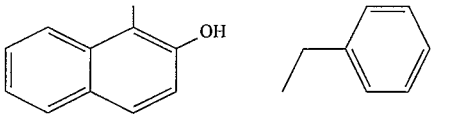 | 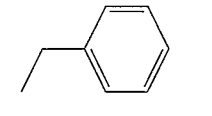 | —COOH | | m/z: 320(M + H) | ((CD₃)₂SO)δ(ppm): 3.20(d, 1H), 3.36(d, 1H), 4.76(t, 1H), 6.79(d, 1H), 7.22(m, 5H), 7.40(t, 1H), 7.65(d, 1H), 7.75(d, 1H), 7.89(d, 1H), 8.92(s, 1H) |
| 55 | 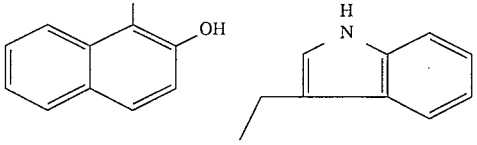 | 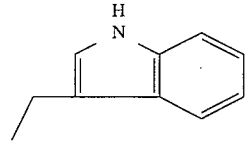 | —COOH | | m/z: 359(M + H) | ((CD₃)₂SO)δ(ppm): 3.40(dd, 2H), 4.77(t, 1H), 6.74(d, 1H), 7.00(t, 1H), 7.09(t, 1H), 7.16(s, 1H), 7.17(t, 1H), 7.33(d, 1H), 7.34(t, 1H), 7.62(dd, 2H), 7.72(dd, 2H), 8.85(s, 1H) |
| 56 | 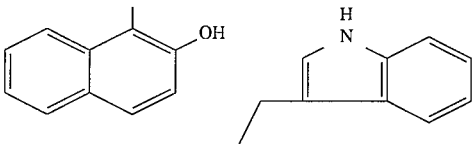 | 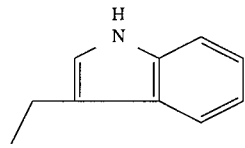 | —H | | m/z: 315(M + H) | |
| 57 | 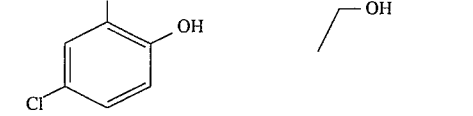 | 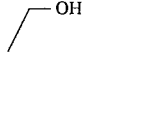 | —COOH | | m/z: 244(M + H) | |
| 58 | 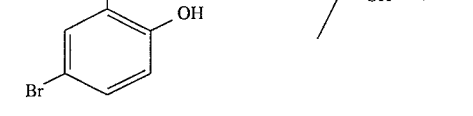 | 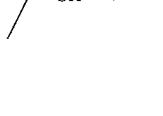 | —COOH | | m/z: 288(M + H) | |
| 59 | 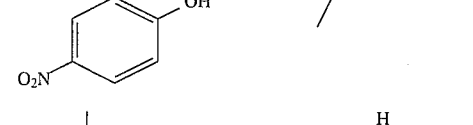 | 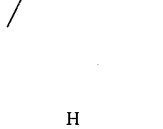 | —COOH | | m/z: 255(M + H) | |
| 60 |  | 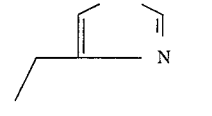 | —COOH | 206~209° C. | m/z: 260(M + H) | ((CD₃)₂SO)δ(ppm): 2.96(dd, 2H), 4.31(t, 1H), 6.76(s, 1H), 6.85(t, 1H), 6.87(d, 1H), 7.33(t, 1H), 7.37(d, 1H), 7.59(s, 1H), 8.32(s, 1H) |
| 61 | 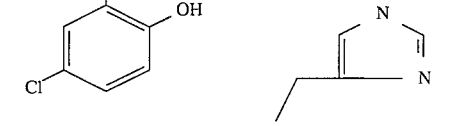 | 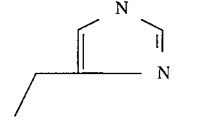 | —COOH | | m/z: 294(M + H) | |

TABLE 2-continued $$\text{Ar}-\text{CH}=\text{N}-\text{CH}(\text{R}_{16})-\text{Y}$$

| Syn. ex. | Ar | R₁₆ | Y | m.p. | MS | NMR |
|---|---|---|---|---|---|---|
| 62 | 2-OH, 5-Br, 3-I phenyl | CH₂-pyridyl (with NH) | —COOH | | m/z: 338(M + H) | |
| 63 | 2-OH, 3-OCH₃, 6-I phenyl | CH₂-pyridyl (with NH) | —COOH | | m/z: 290(M + H) | |
| 64 | 2-OH, 4-Cl, 3-I phenyl | CH(CH₃)₂ | —COOH | 148–149° C. | m/z: 256(M + H) | ((CD₃)₂SO)δ(ppm): 0.90(d, 6H), 2.28(m, 1H), 3.88(d, 1H), 6.94(d, 1H), 7.34(d, 1H), (s, 1H), 8.54(s, 1H) |

TABLE 3

| Syn. ex. | Structural formula | m.p. | MS | NMR |
|---|---|---|---|---|
| 65 | 2-hydroxynaphthalen-1-yl-CH=N-CH₂CH₂-SO₃H | | m/z: 280(M + H) | |
| 66 | 2-hydroxynaphthalen-1-yl-CH=N-CH₂-C(=O)-NH-CH₂-COOH | | m/z: 287(M + H) | ((CD₃)₂SO)δ(ppm): 3.85(d, 3H), 4.40(s, 2H), 6.77(d, 1H), 7.22(t, 1H), 7.44(t, 1H), 7.66(d, 1H), 7.75(d, 1H), 8.07(d, 1H), 9.09(s, 1H) |
| 67 | 2-hydroxynaphthalen-1-yl-CH=N-CH(CH₂COOH)-C(=O)-NH-CH(CH₂Ph)-COOCH₃ | | m/z: 449(M + H) | |

SYNTHESIS EXAMPLE 68

To a 1N solution of sodium hydroxide in methanol (60 ml) were added L-histidine (4 g) and pyridoxal hydrochloride (5.5 g) and the mixture was stirred for 5 days to give N-pyridoxilidene-L-histidine-sodium salt (7 g).

The measured results of the melting point, mass spectrum and NMR spectrum of the resulting compound are listed in Table 4 below.

SYNTHESIS EXAMPLE 69 TO 72

In the same way as described in Synthesis Example 68, the compounds shown in Table 4 were prepared. The measured results of the melting point, mass spectrum and NMR spectrum of each compound are listed in Table 4.

TABLE 4

$$Ar-CH=N-CH(R_{17})-COOH$$

| Syn ex. | Ar | $R_{17}$ | m.p. | MS | NMR |
|---|---|---|---|---|---|
| 68 | HO-[pyridine with OH, CH3, N]- | -CH2-CH=CH-(1H-imidazol-N) | 153–155° C. | m/z: 349(M+H) (as 2Na salt) | (D$_2$O)δ(ppm): 2.30(s, 3H), 3.18(dd, 2H), 4.21(d, 1H), 4.70(s, 2H), 7.55(s, 1H), 7.57(s, 1H), 7.71(s, 1H), 7.78(s, 1H) |
| 69 | HO-[pyridine with OH, CH3, N]- | -CH2-OH | 92–95° C. | m/z: 299(M+H) (as 2Na salt) | (D$_2$O)δ(ppm): 2.43(s, 3H), 4.12(dd, 2H), 4.51(t, 1H), 4.88(s, 2H), 7.63(s, 1H), 8.98(s, 1H) |
| 70 | HO-[pyridine with OH, CH3, N]- | -CH2-C6H4-OH | 151–153° C. | m/z: 375(M+H) (as 2Na salt) | (D$_2$O + NaOD)δ(ppm): 2.28(s, 3H), 2.72(m, 2H), 3.37(t, 1H), 4.89(s, 2H), 6.52(d, 2H), 6.95(d, 2H), 7.42(s, 1H), 8.49(s, 1H) |
| 71 | HO-[pyridine with OH, CH3, N]- | -CH2CH2-COOH | 162–163° C. | m/z: 411(M+H) (as 3K salt) | (D$_2$O)δ(ppm): 2.06(m, 2H), 2.35(t, 2H), 2.39(s, 3H), 4.29(t, 1H), 4.73(s, 2H), 7.55(s, 1H), 8.83(s, 1H) |
| 72 | HO-[pyridine with OH, CH3, N]- | -CH(CH$_3$)C$_2$H$_5$ | 127–129° C. | m/z: 357(M+H) (as 2K salt) | (D$_2$O)δ(ppm): 0.94(t, 3H), 1.00(d, 3H), 1.38(m, 2H), 2.07(m, 1H), 2.39(s, 3H), 4.21(d, 1H), 4.72(d, 2H), 7.49(s, 1H), 8.77(s, 1H) |

TEST EXAMPLE 1

Test for Inhibitory Effects on UV-induced Lipid Peroxidation

The test was carried out on the basis of the methods described in Biochim. Biophys. Act., Vol. 1084, page 261, 1991 and Method in Enzymol., Vol. 52, page 302, 1978. Namely, 12 μl of an aqueous sodium hydroxide solution of each of the test compounds shown in Table 5 below was added to 1.2 ml of a homogenate of murine swiss 3T3 cells (i.e. a kind of murine skin cells) prepared by a conventional method in 20 mM phosphate buffer (protein content: 1.5 to 1.8 mg/ml). The final concentration of the test compounds was adjusted to be 1 mM and the pH of the solution was adjusted to 7.2 to 7.8. If test compounds were not soluble in an aqueous sodium hydroxide solution, they were dissolved in N,N-dimethyl sulfoxide (DMSO).

This solution (1.1 ml) was irradiated with UV rays (0.4 mW/cm$^2$, 90 min.) using a UVB lamp "EB-280C/J" (manufactured by Spectronics). To an aliquot (1.0 ml) of this solution were successively added 0.2 ml of an aqueous solution of sodium dodecyl sulfate and 1.0 ml of an aqueous solution of thiobarbituric acid/trichloroacetic acid/hydrochloric acid, and the mixed solution was heated in a boiling water bath for 15 minutes. After ice-cooling, the solution was extracted with 1.0 ml of 1-butanol to prepare a sample for determining peroxide lipid as absorbance at a wavelength of 535 nm using a spectrophotometer "Model 320" (manufactured by Hitachi).

The percent inhibition of lipid peroxidation of the test compounds was calculated from the following equation (1) and the results are shown in Table 5.

$$\% \text{ Peroxidation inhibition} = \left(1 - \frac{A_1 - A_3}{A_2 - A_3}\right) \times 100 \quad (1)$$

$A_1$: Absorbance when a test compound was added.

$A_2$: Absorbance when a test compound was not added.

$A_3$: Absorbance when a test compound was not added and UV rays were not irradiated.

TABLE 5

| | Test compounds | % Inhibition |
|---|---|---|
| Example | Compound of Synthesis Example 1 | 40 |
| | Compound of Synthesis Example 2 | 59 |
| | Compound of Synthesis Example 3 | 65 |
| | Compound of Synthesis Example 4 | 60 |
| | Compound of Synthesis Example 5 | 52 |
| | Compound of Synthesis Example 6 | 66 |
| | Compound of Synthesis Example 7 | 48 |
| | Compound of Synthesis Example 8 | 60 |
| | Compound of Synthesis Example 9 | 60 |
| | Compound of Synthesis Example 10 | 56 |
| | Compound of Synthesis Example 11 | 77 |
| | Compound of Synthesis Example 12 | 29 |
| | Compound of Synthesis Example 13 | 53 |
| | Compound of Synthesis Example 14 | 45 |
| | Compound of Synthesis Example 15 | 51 |
| | Compound of Synthesis Example 28 | 20 |
| Comparative Example | EDTA | 34 |
| | Citric acid | 19 |
| | Vitamin C | −686 |

TEST EXAMPLE 2

Test for Inhibitory Effects on Hydroxyl Radical Formation (1)

The test was carried out in accordance with the method described in FEBS Letters, Vol. 128, page 347, 1981. Namely, to 1.1 ml of a solution of 54 mM sodium chloride in 9 mM phosphate buffer (hereinafter referred to as "PBS-1") were successively added 140 µl of a solution of each of the test compounds shown in Table 6 below in PBS-1, 5 µl of a 1 mM solution of ammonium iron (III) sulphate in hydrochloric acid, 140 µl of a solution of xanthine (manufactured by Tokyo Kasei Co.) in PBS-1, 14 µl a solution of deoxyribose (Sigma) in PBS-1 and xanthine oxidase (Sigma). The final concentrations of the test compounds, ammonium iron (III) sulphate, xanthine, deoxyribose and xanthine oxidase were adjusted to be 360 µM, 36 µM, 70 µM, 700 µM and 0.7 unit/ml, respectively. If test compounds were not soluble in PBS-1 alone, aqueous sodium hydroxide solution or DMSO was added. The pH of the solution was adjusted to 7.4 to 7.8.

After this solution was maintained at 37° C. for 15 minutes, 1 ml of an aqueous sodium hydroxide solution of thiobarbituric acid and 1 ml of acetic acid were successively added, and the mixed solution was heated in a boiling water bath for 10 minutes, then ice-cooled to prepare a sample for determining the hydroxyl radical at an excitation wavelength of 532 nm and a fluorescent wavelength of 553 nm using a fluorecent spectrophotometer "Model F-4000" (manufactured by Hitachi). The percent inhibition of the hydroxyl radical was calculated from the following equation (2) and the results are shown in Table 6.

$$\% \text{ Inhibition of hydroxy radical} = \left(1 - \frac{F_1 - F_2}{F_3 - F_4}\right) \times 100 \quad (2)$$

$F_1$: Intensity of fluorescence when a test compound was added.
$F_2$: Intensity of fluorescence when a test compound was added but deoxyribose was not added.
$F_3$: Intensity of fluorescence when a test compound was not added.
$F_4$: Intensity of fluorescence when neither test compound nor deoxyribose was added.

TABLE 6

| | Test compounds | % Inhibition |
| --- | --- | --- |
| Example | Compound of Syn. Example 1 | 29 |
| | Compound of Syn. Example 2 | 29 |
| | Compound of Syn. Example 3 | 15 |
| | Compound of Syn. Example 4 | 33 |
| | Compound of Syn. Example 18 | 42 |
| | Compound of Syn. Example 28 | 19 |
| | Compound of Syn. Example 31 | 16 |
| | Compound of Syn. Example 68 | 15 |
| | Compound of Syn. Example 69 | 36 |
| | Compound of Syn. Example 70 | 60 |
| Comparative Example | EDTA | −121 |
| | Citric acid | −33 |

TEST EXAMPLE 3

Test for Inhibitory Effects on Metal Ion-induced Lipid Peroxidation

The test was carried out according to the method described in Method in Enzymol., Vol. 52, page 302, 1978. A C57 black mouse was killed by cervical dislocation, and the whole brain extracted from the dissected head was washed with 20 mM phosphate buffer (hereinafter referred to as "PBS-2"). Then, the brain was added with PBS-2 in an amount of 19 times its wet weight, and the mixture was disrupted and homogenized with a homogenizer "Polytron" (manufactured by Kinematica). The thus prepared 5% solution of the murine brain homogenate in PBS-2 was diluted 1:5 with fresh PBS-2. To 800 µl of the resulting 1% solution of the murine brain homogenate in PBS-2 (protein content: 0.8 to 1.0 mg/ml) were successively added 100 µl of a PBS-2 solution of each of the test compounds shown in Table 7 below and 100 µl of an aqueous solution of ammonium iron (II) sulphate. The final concentration of the test compounds and ammonium iron (II) sulphate were adjusted to be 1 mM and 100 µM, respectively. If test compounds were not soluble in PBS-2 alone, an aqueous sodium hydroxide solution or DMSO was added. The pH of the solution was adjusted to 7.2 to 7.8.

The solution after heated at 37° C. for 30 minutes was added with 2.0 ml of an aqueous solution of thiobarbituric acid/trichloroacetic acid/hydrochloric acid, and the mixture was heated in a boiling water bath for 15 minutes. After ice-cooling, the solution was extracted with 1.0 ml of 1-butanol to prepare a sample for determining the peroxide lipid in the same way as described in Test Example 1.

The percent inhibition of lipid peroxidation of the test compounds was calculated from the following equation (3) and the results are shown in Table 7.

$$\% \text{ Peroxidation Inhibition} = \left(1 - \frac{A_1 - A_3}{A_2 - A_3}\right) \times 100 \quad (3)$$

$A_1$: Absorbance when a test compound was added.
$A_2$: Absorbance when a test compound was not added.
$A_3$: Absorbance when a test compound was not added and heating at 37° C. for 30 minutes was not carried out.

TABLE 7

| | Test compounds | % Inhibition |
| --- | --- | --- |
| Example | Compound of Syn. Example 1 | 26 |
| | Compound of Syn. Example 2 | 41 |
| | Compound of Syn. Example 3 | 21 |
| | Compound of Syn. Example 4 | 26 |
| | Compound of Syn. Example 18 | 26 |
| | Compound of Syn. Example 27 | 87 |
| | Compound of Syn. Example 28 | 80 |
| | Compound of Syn. Example 29 | 78 |
| | Compound of Syn. Example 30 | 43 |
| | Compound of Syn. Example 31 | 90 |
| | Compound of Syn. Example 32 | 83 |
| | Compound of Syn. Example 33 | 95 |
| | Compound of Syn. Example 34 | 57 |
| | Compound of Syn. Example 35 | 16 |
| | Compound of Syn. Example 36 | 80 |
| | Compound of Syn. Example 37 | 30 |
| | Compound of Syn. Example 38 | 74 |
| | Compound of Syn. Example 39 | 50 |
| | Compound of Syn. Example 40 | 88 |
| | Compound of Syn. Example 41 | 79 |
| | Compound of Syn. Example 42 | 86 |
| | Compound of Syn. Example 43 | 40 |
| | Compound of Syn. Example 44 | 90 |
| | Compound of Syn. Example 45 | 85 |
| | Compound of Syn. Example 46 | 80 |
| | Compound of Syn. Example 47 | 90 |
| | Compound of Syn. Example 48 | 85 |
| | Compound of Syn. Example 49 | 81 |
| | Compound of Syn. Example 50 | 85 |
| | Compound of Syn. Example 51 | 84 |
| | Compound of Syn. Example 52 | 100 |
| | Compound of Syn. Example 53 | 96 |
| | Compound of Syn. Example 54 | 83 |

TABLE 7-continued

| Test compounds | | % Inhibition |
|---|---|---|
| | Compound of Syn. Example 55 | 87 |
| | Compound of Syn. Example 56 | 57 |
| | Compound of Syn. Example 57 | 44 |
| | Compound of Syn. Example 58 | 40 |
| | Compound of Syn. Example 59 | 11 |
| | Compound of Syn. Example 60 | 34 |
| | Compound of Syn. Example 61 | 45 |
| | Compound of Syn. Example 62 | 45 |
| | Compound of Syn. Example 63 | 60 |
| | Compound of Syn. Example 64 | 60 |
| | Compound of Syn. Example 65 | 73 |
| | Compound of Syn. Example 66 | 20 |
| | Compound of Syn. Example 67 | 38 |
| | Compound of Syn. Example 68 | 15 |
| | Compound of Syn. Example 69 | 23 |
| | Compound of Syn. Example 70 | 27 |
| | Compound of Syn. Example 71 | 13 |
| | Compound of Syn. Example 72 | 14 |
| Comparative Example | Citric acid | −15 |
| | Vitamin C | −23 |
| | Vitamin E | 29 |

TEST EXAMPLE 4

Test for Inhibitory Effects on Lipid Peroxidation

To 900 µl of a 5% solution of the murine brain homogenate in PBS-2 prepared in the same way as described in Test Example 3 was added 100 µl of a PBS-2 solution of each of the test compounds shown in Table 8 below. The final concentration of the test compounds was adjusted to be 30 µM. If test compounds were not soluble in PBS-2 alone, an aqueous solution of sodium hydroxide or DMSO was added. The pH of the solution was adjusted to 7.2 to 7.8.

The solution after heated at 37° C. for 60 minutes was added with 1.0 ml of an aqeuous solution of thiobarbituric acid/trichloroacetic acid/hydrochloric acid, and the mixture was heated in a boiling water bath for 15 minutes. After ice-cooling, the solution was extracted with 2.0 ml of 1-butanol to prepare a sample for determining the lipid peroxide in the same way as described in Test Example 1. The percent inhibition of lipid peroxidation of the test compounds was calculated from the following equation (4), and the results are shown in Table 8.

$$\% \text{ Peroxidation inhibition} = \left( 1 - \frac{A_4 - A_6}{A_5 - A_6} \right) \times 100 \quad (4)$$

$A_4$: Absorbance when a test compound was added.
$A_5$: Absorbance when a test compound was not added.
$A_6$: Abosrbance when a test compound was not added and heating at 37° C. for 90 minutes was not carried out.

TABLE 8

| | Test compounds | % Inhibition |
|---|---|---|
| Example | Compound of Syn. Example 1 | 53 |
| | Compound of Syn. Example 2 | 26 |
| | Compound of Syn. Example 16 | 89 |
| | Compound of Syn. Example 17 | 56 |
| | Compound of Syn. Example 18 | 44 |
| | Compound of Syn. Example 19 | 59 |
| | Compound of Syn. Example 20 | 91 |
| | Compound of Syn. Example 21 | 90 |
| | Compound of Syn. Example 22 | 91 |
| | Compound of Syn. Example 23 | 39 |
| | Compound of Syn. Example 24 | 85 |
| | Compound of Syn. Example 25 | 55 |

TABLE 8-continued

| | Test compounds | % Inhibition |
|---|---|---|
| | Compound of Syn. Example 26 | 39 |
| | Compound of Syn. Example 27 | 98 |
| | Compound of Syn. Example 28 | 70 |
| | Compound of Syn. Example 69 | 15 |
| | Compound of Syn. Example 71 | 29 |
| Comparative Example | Citric acid | −13 |
| | Vitamin C | −22 |
| | Vitamin E | 30 |

TEST EXAMPLE 5

Test for Inhibitory Effects on Hydroxyl Radical Formation (2)

To 75 µl of a solution of each of the test compounds shown in Table 9 below in 0.1M phosphate buffer (hereinafter referred to as "PBS-3") were successively added 75 µl of an aqueous solution of iron (II) sulphate, 20 µl of an aqueous solution of 5,5-dimethyl-1-pyrroline-N-oxide "DMPO" (manufactured by Dojin Chemical) and 75 µl of an aqueous solution of hydrogen peroxide. The final concentration of the test compounds, iron (II) sulphate, DMPO and hydrogen peroxide were adjusted to be 306 µM, 306 µM, 75 mM and 306 µM, respectively. If test compounds were not soluble in PBS-3 alone, an aqueous sodium hydroxide solution or N,N-dimethyl formamide was added.

This solution was subjected to determination for the hydroxy radical immediately (within 40 seconds), using an electron spin resonance (ESR) meter "JES-FR80S" (manufactured by Nippon Denshi).

The percent inhibition of hydroxy radicals was calculated from the equation (5), and the results are shown in Table 9.

$$\% \text{ Inhibition of hydroxy radicals} = \left( 1 - \frac{E_1}{E_2} \right) \times 100 \quad (5)$$

$E_1$: Signal magnitude when a test compound was added.
$E_2$: Signal magnitude when a test compound was not added.

TABLE 9

| | Test compounds | % Inhibition |
|---|---|---|
| Example | Compound of Syn. Example 1 | 27 |
| | Compound of Syn. Example 2 | 44 |
| | Compound of Syn. Example 3 | 45 |
| | Compound of Syn. Example 4 | 27 |
| | Compound of Syn. Example 16 | 56 |
| | Compound of Syn. Example 18 | 43 |
| | Compound of Syn. Example 22 | 51 |
| | Compound of Syn. Example 27 | 71 |
| | Compound of Syn. Example 28 | 56 |
| | Compound of Syn. Example 29 | 60 |
| | Compound of Syn. Example 30 | 25 |
| | Compound of Syn. Example 47 | 32 |
| | Compound of Syn. Example 48 | 54 |
| | Compound of Syn. Example 52 | 43 |
| | Compound of Syn. Example 53 | 68 |
| | Compound of Syn. Example 60 | 33 |
| | Compound of Syn. Example 68 | 10 |
| | Compound of Syn. Example 69 | 19 |
| | Compound of Syn. Example 70 | 28 |
| | Compound of Syn. Example 71 | 21 |
| Comparative Example | EDTA | −142 |

TEST EXAMPLE 6

Test for UV Absorptive Activities

A solution of each of the test compounds shown in Table 10 below in ethanol was prepared for the final concentration to be 100 μM. If test compounds were not soluble in ethanol alone, water or DMSO was added.

The absorption spectrum of each sample was determined using a spectrophotometer "Model 320" (manufactured by Hitachi). The molar extinction coefficient in the both of UVA and UVB regions are shown in Table 10.

TABLE 10

|  | Test compounds | Wavelength (nm) of maximum absorption | Maximum molar extinction coefficient |
|---|---|---|---|
| Example | Compound of Syn. Example 18 | 290 | 3,500 |
|  | Compound of Syn. Example 22 | 290 | 5,300 |
|  | Compound of Syn. Example 27 | 309 | 7,000 |
|  | Compound of Syn. Example 28 | 307 | 10,000 |
|  | Compound of Syn. Example 68 | 291 | 4,300 |
|  | Compound of Syn. Example 69 | 336 | 3,000 |

This invention is further illustrated by the following use examples, in which the proportions of the components are expressed as % by weight.

USE EXAMPLE 1

(Skin cream)

Components 1 and 2 shown in Table 11 below were heated to 80° C. and 50° C., respectively, and the Component 2 was gradually added in portions to the Component 1 with stirring, to form an emulsion. Component 3 was added at 50° C. with stirring under water-cooling, and then the mixture was cooled to 35° C. to give a desired product.

The product where the compound of Synthetis Example 1 was incorporated was a highly skin-protective skin cream with anti-active oxygen property. This skin cream had gloss, high opacity and good feel on skin.

TABLE 11

|  | Components | Proportion |
|---|---|---|
| 1 | Squalane | 13.0 |
|  | Cetyl octanoate | 13.0 |
|  | Di (cholesteryl, octyldodecyl)-N-lauroyl-L-glutamic acid ester | 5.0 |
|  | Compound of Synthesis Example 1 | 2.0 |
|  | Hardened oil | 5.0 |
|  | Behenyl alcohol | 1.0 |
|  | Stearic acid | 2.0 |
|  | Self-emulsifiable glycerin monostearate | 4.0 |
|  | Diglycerin oleate | 1.0 |
|  | Dimethyl polysiloxane | 0.3 |
| 2 | Preservatives | 0.2 |
|  | Sodium N-stearoyl-L-glutamate | 0.4 |
|  | Xanthane gum | 0.05 |
|  | 1,3-Butylene glycol | 7.0 |
|  | Purified water | 45.85 |
| 3 | Perfume | 0.2 |

USE EXAMPLE 2

(Skin milk)

Component 1 shown in Table 12 below was heated to 85° C. Component 2 was gradually added in portions to the Component 1 with stirring, and then Component 3 was added. The mixture was water-cooled to 30° C. with stirring to give a desired product.

This skin milk where the compound of Synthesis Example 1 was incorporated had a skin protective activity attributable to the anti-active oxygen property of the compound.

TABLE 12

|  | Components | Proportion |
|---|---|---|
| 1 | Squalane | 13.0 |
|  | Compound of Synthesis Example 1 | 2.0 |
|  | Isocetyl octanoate | 9.0 |
|  | Glycerin trioctanoate | 4.0 |
|  | Propylene glycol stearate | 0.5 |
|  | Behenyl alcohol | 0.5 |
|  | Stearic acid | 1.0 |
|  | Lipophilic glycerin monostearate | 1.0 |
|  | Diglycerin oleate | 0.5 |
|  | Polyethylene glycol stearate | 2.5 |
| 2 | Preservative | 0.2 |
|  | Carboxyvinyl polymer (1.0% aqueous solution) | 15.0 |
|  | Oleylphosphoric acid | 0.4 |
|  | 1,3-Butylene glycol | 5.0 |
|  | Purified water | 44.9 |
| 3 | L-Arginine | 0.3 |
|  | Purified water | 0.2 |

USE EXAMPLE 3

(Lotion)

The components shown in Table 13 below were homogeneously dissolved to prepare a lotion.

This lotion where the compound of Synthesis Example 5 was incorporated had a skin-protective activity attributable to the anti-active oxygen property of the compound.

TABLE 13

| Components | Proportion |
|---|---|
| Methylparabin | 0.2 |
| Sodium pyrrolidone-2-carboxylate | 2.0 |
| 1,3-Butylene glycol | 5.0 |
| Compound of Synthesis Example 5 | 0.2 |
| Purified water | 92.6 |

INDUSTRIAL APPLICABILITY

As is evident from the above Examples, the anti-active oxygen agents according to this invention produce high inhibitory effects on the action of active oxygen species and can be easily prepared at low costs. They are physically and chemically stable. Accordingly, they can be used in anti-skin aging agents, cosmetics, pharmaceuticals or foods in order to prevent active oxygen species-induced disorders and diseases in human or other bodies as well as denaturation and deterioration of foods. Moreover, some of the anti-active oxygen compounds according to this invention have a UV absorptive power so that they are especially useful in cosmetics or the like.

I claim:

1. A method for inhibiting the generation of active oxygen species in a material, comprising applying an effective amount of an amino acid derivative represented by the following formula (I):

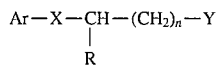

wherein Ar represents a 2-hydroxy-1-naphthyl or pyridyl group, and one or more of the hydrogen atoms attached to the aromatic ring may be independently substituted with a halogen atom, or a C1–6 alkyl, hydroxy, C1–6 hydroxyalkyl, nitro, or C1–6 alkoxyl group; R represents the side chain of an amino acid; X represents —$CH_2$—NH— or —$CH_2$=NH—; Y represents a hydrogen atom, —$COOR^1$, —$SO_3H$, —$CON(R^2)R^3$, —$CONHCH(R^5)COOR^4$ or —$CH_2OH$ (wherein each of $R^1$ to $R^4$ represents a hydrogen atom or a C1–6 alkyl group, and $R^5$ represents the side chain of an amino acid); and n represents an integer of 0 or 1; or its salt.

2. The method of claim 1, wherein said Ar represents 2-methyl-3-hydroxy-5-hydroxymethyl-4-pyridyl group.

3. The method of claim 1, wherein said X represents —$CH_2$—NH—.

4. The method of claim 1, wherein said Y represents —$COOR^1$.

5. The method of claim 1, wherein said n represents integer of 0.

6. A method for treatment against skin aging, comprising applying an effective amount of an amino acid derivative represented by the following formula (I):

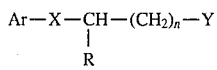

wherein Ar represents a 2-hydroxy-1-naphthyl or pyridyl group, and one or more of the hydrogen atoms attached to the aromatic ring may be independently substituted with a halogen atom, or a C1–6 alkyl, hydroxy, C1–5 hydroxyalkyl, nitro, or C1–6 alkoxyl group; R represents the side chain of an amino acid; X represents —$CH_2$—NH— or —$CH_2$=NH—; Y represents a hydrogen atom, —$COOR^1$, —$SO_3H$, —$CON(R^2)R^3$, —$CONHCH(R^5)COOR^4$ or —$CH_2OH$ (wherein each of $R^1$ to $R^4$ represents a hydrogen atom or a C1–6 alkyl group, and $R^5$ represents the side chain of an amino acid); and n represents an integer of 0 or 1; or its salt.

7. A method for inhibiting the generation of active oxygen species in a material, comprising applying an effective amount of an amino acid derivative represented by the following formula (I):

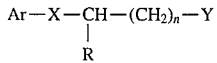

wherein Ar represents a 2-hydroxyphenyl group, and one or more of the hydrogen atoms attached to the aromatic ring may be independently substituted with a halogen atom, or a C1–6 alkyl, hydroxy, C1–6 hydroxyalkyl, nitro, or C1–6 alkoxyl group; R represents the side chain of an amino acid; X represents —$CH_2$—NH—; Y represents a hydrogen atom, —$COOR^1$, —$SO_3H$, —$CON(R^2)R^3$, —$CONHCH(R^5)COOR^4$ or —$CH_2OH$ (wherein each of $R^1$ to $R^4$ represents a hydrogen atom or a C1–6 alkyl group, and $R^5$ represents the side chain of an amino acid); and n represents an integer of 0 or 1; or its salt.

8. A method for inhibiting the generation of active oxygen species in a material, comprising applying an effective amount of an amino acid derivative represented by the following formula (I):

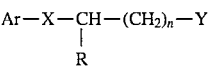

wherein Ar represents a 2-hydroxyphenyl group, and one or more of the hydrogen atoms attached to the aromatic ring may be independently substituted with a halogen atom, or a C1–6 alkyl, hydroxy, C1–6 hydroxyalkyl, nitro, or C1–6 alkoxyl group; R represents the side chain of histidine, serine, homoserine, tyrosine, 3,4-dihydroxyphenylalanine, glutamic acid, aspartic acid, lysine, threonine, glutamine, asparagine, arginine, phenylalanine or tryptophan; X represents —CH=N—; Y represents a hydrogen atom, —$COOR^1$, —$SO_3H$, —$CON(R^2)R^3$, —$CONHCH(R^5)COOR^4$ or —$CH_2OH$ (wherein each of $R^1$ to $R^4$ represents a hydrogen atom or a C1–6 alkyl group, and $R^5$ represents the side chain of an amino acid); and n represents an integer of 0 or 1; or its salt.

9. The method of claim 6, wherein said Ar represents 2-methyl-3-hydroxy-5-hydroxymethyl-4-pyridyl group.

10. The method of claim 6, wherein said X represents —$CH_2$—NH—.

11. The method of claim 6, wherein said Y represents —$COOR^1$.

12. The method of claim 6, wherein said n represents integer of 0.

13. A method for treatment against skin aging, comprising applying an effective amount of an amino acid derivative represented by the following formula (I):

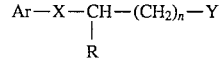

wherein Ar represents a 2-hydroxyphenyl group, and one or more of the hydrogen atoms attached to the aromatic ring may be independently substituted with a halogen atom, or a C1–6 alkyl, hydroxy, C1–6 hydroxyalkyl, nitro, or C1–6 alkoxyl group; R represents the side chain of an amino acid; X represents —$CH_2NH$—; Y represents a hydrogen atom, —$COOR^1$, —$SO_3H$, —$CON(R^2)R^3$, —$CONHCH(R^5)COOR^4$ or —$CH_2OH$ (wherein each of $R^1$ to $R^4$ represents a hydrogen atom or a C1–6 alkyl group, and $R^5$ represents the side chain of an amino acid); and n represents an integer of 0 or 1; or its salt.

14. A method for treatment against skin aging, comprising applying an effective amount of an amino acid derivative represented by the following formula (I):

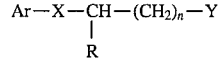

wherein Ar represents a 2-hydroxyphenyl group, and one or more of the hydrogen atoms attached to the aromatic ring may be independently substituted with a halogen atom, or a C1–6 alkyl, hydroxy, C1–6 hydroxyalkyl, nitro, or C1–6 alkoxyl group; R represents the side chain of histidine, serine, homoserine, tyrosine, 3,4-dihydroxyphenylalanine, glutamic acid, aspartic acid, lysine, threonine, glutamine, asparagine, arginine, phenylalanine or tryptophan; X represents —CH=N—; Y represents a hydrogen atom, —$COOR^1$, —$SO_3H$, —$CON(R^2)R^3$, —$CONHCH(R^5)COOR^4$ or —$CH_2OH$ (wherein each of $R^1$ to $R^4$ represents a hydrogen atom or a C1–6 alkyl group, and $R^5$ represents the side chain of an amino acid); and n represents an integer of 0 or 1; or its salt.

15. An amino acid derivative represented by following general formula (II):

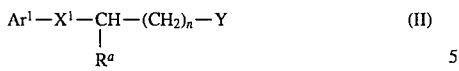

wherein $Ar^1$ represents a 2-hydroxyphenyl group, and one or more of the hydrogen atoms attached to the aromatic ring may be independently substituted with a halogen atom, or an alkyl, hydroxy, hydroxyalkyl, nitro, or alkoxyl group; $R^a$ represents the side chain of valine, leucine, isoleucine, glutamic acid, glutamine, asparagine, arginine, lysine, threonine, tyrosine, tryptophan, homoserine, 3,4-dihydroxyphenylalanine, or a hydrogen atom; $X^1$ represents $-CH_2-NH-$; Y represents a hydrogen atom, $-COOR^1$, $-SO_3H$, $-CON(R^2)R^3$ or $-CONHCH(R^5)COOR^4$ (wherein each of $R^1$ to $R^4$ represents a hydrogen atom or a C1–6 alkyl group, and $R^5$ represents the side chain of an amino acid); and n represents an integer of 0 or 1; or its salt.

16. An amino acid derivative represented by following general formula (III):

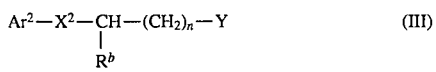

wherein $Ar^2$ represents a 2-hydroxy-1-naphthyl group, and one or more of the hydrogen atoms attached to the aromatic ring may be independently substituted with a halogen atom, or an alkyl, hydroxy, hydroxyalkyl, nitro, or alkoxyl group; $R^b$ represents the side chain of glutamine, asparagine, histidine, cysteine, serine, threonine, tyrosine, tryptophan, homoserine, 3,4-dihydroxyphenylalanine, or a hydrogen atom; $X^2$ represents $-CH=N-$; Y represents a hydrogen atom, $-COOR^1$, $-SO_3H$, or $-CON(R^2)R^3$, $-CONHCH(R^5)COOR^4$ or $-CH_2OH$ (wherein each of $R^1$ to $R^4$ represents a hydrogen atom or a C1–6 alkyl group, and $R^5$ represents the side chain of an amino acid); and n represents an integer of 0 or 1; or its salt.

17. The amino acid derivative of claim 15, wherein said $Ar^1$ represents 2-hydroxyphenyl group.

18. The amino acid derivative of claim 17, wherein said Y represents $-COOH$.

19. The amino acid derivative of claim 17, wherein said n represents integer of 0.

20. The amino acid derivative of claim 16, wherein said $Ar^2$ represents 2-hydroxy-1-naphthyl group.

21. The amino acid derivative of claim 20, wherein said Y represents $-COOR^1$.

22. The amino acid derivative of claim 20, wherein said n represents integer of 0.

* * * * *

UNITED STATES PATENT AND TRADEMARK OFFICE
CERTIFICATE OF CORRECTION

PATENT NO. : 5,594,012
DATED : January 14, 1997
INVENTOR(S) : Manabu KITAZAWA, et al.

It is certified that error appears in the above-identified patent and that said Letters Patent is hereby corrected as shown below:

Columns 3 and 4, TABLE 1, number 1,

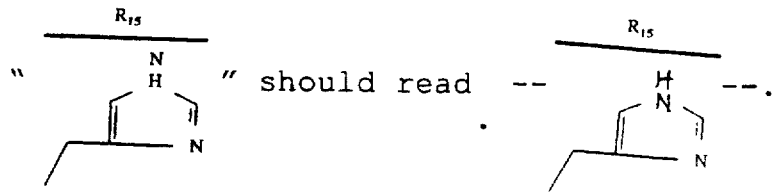

Columns 7 and 8, TABLE 1 continued, number 15,

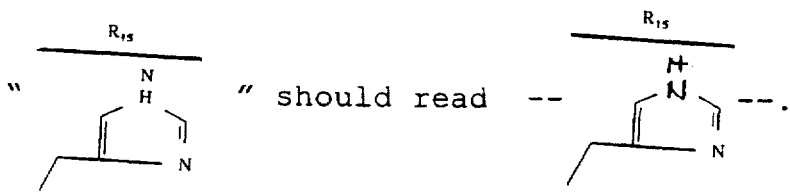

UNITED STATES PATENT AND TRADEMARK OFFICE
CERTIFICATE OF CORRECTION

PATENT NO. : 5,594,012
DATED : January 13, 1997
INVENTOR(S) : Manabu KITAZAWA, et al.

It is certified that error appears in the above-identified patent and that said Letters Patent is hereby corrected as shown below:

Columns 19 and 20, TABLE 4, number 68,

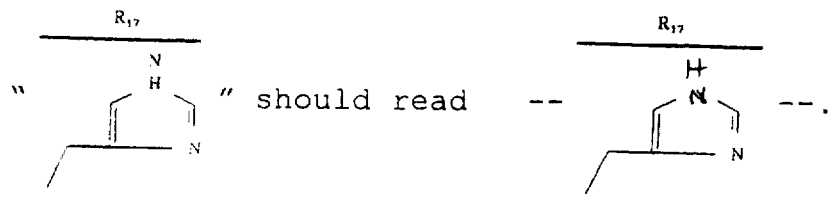

Signed and Sealed this

Fourth Day of May, 1999

Attest:

Q. TODD DICKINSON

*Attesting Officer*  *Acting Commissioner of Patents and Trademarks*